(12) United States Patent
Connolly

(10) Patent No.: US 11,079,351 B2
(45) Date of Patent: Aug. 3, 2021

(54) ACTIVE ENZYME PROTECTION SYSTEM FOR AN ELECTROCHEMICAL BIOSENSOR

(71) Applicant: Jim Connolly, Indianapolis, IN (US)

(72) Inventor: Jim Connolly, Indianapolis, IN (US)

(*) Notice: Subject to any disclaimer, the term of this patent is extended or adjusted under 35 U.S.C. 154(b) by 0 days.

(21) Appl. No.: 16/194,489

(22) Filed: Nov. 19, 2018

(65) Prior Publication Data

US 2019/0317039 A1 Oct. 17, 2019

Related U.S. Application Data

(60) Provisional application No. 62/589,639, filed on Nov. 22, 2017.

(51) Int. Cl.
*G01N 27/327* (2006.01)
*C12Q 1/00* (2006.01)

(52) U.S. Cl.
CPC ......... *G01N 27/3272* (2013.01); *C12Q 1/001* (2013.01)

(58) Field of Classification Search
CPC .......... G01N 27/3271–3278; C12Q 2521/537; C12Q 1/00–008
USPC ..... 204/403.01–403.15; 205/777.5–778, 792
See application file for complete search history.

(56) References Cited

U.S. PATENT DOCUMENTS

| 6,127,138 A * | 10/2000 | Ishimaru ............... C12N 9/62 435/23 |
| 8,673,646 B2 | 3/2014 | Yuan et al. |
| 2004/0063213 A1 | 4/2004 | Hirai et al. |
| 2010/0025264 A1 * | 2/2010 | Yuan ............... G01N 33/5438 205/777.5 |
| 2018/0163184 A1 * | 6/2018 | Huang ................. C12Q 1/26 |

FOREIGN PATENT DOCUMENTS

| EP | 1693461 | 8/2006 |
| EP | 1914315 | 4/2008 |
| JP | 2006061019 | 3/2006 |
| JP | 2009171874 | 8/2009 |
| WO | 2017038956 | 3/2017 |

OTHER PUBLICATIONS

Bacillus, Neutral Proteinase, Toyobo Enzymes industrial Grade, p. 285-287, Toyobo USA, Inc., New York, (prior to Nov. 16, 2018).
Patent Cooperation Treaty, Int'l Search Report & Written Opinion, Form PCT/ISA/220 (dated Jul. 2017).

* cited by examiner

*Primary Examiner* — Bach T Dinh
(74) *Attorney, Agent, or Firm* — Blanchard & Associates

(57) ABSTRACT

Immobilization zones through which a sample flows before reaching the proteolytic agents and/or active enzyme and associated electrode/s of an electrochemical test sensor may be used to trap or chemically deactivate active enzyme and/or proteolytic agent deactivating agents. Through either trapping or chemical deactivation, the immobilization zones substantially prevent the enzyme deactivating agents from reaching, and thus reducing the activity of the active enzyme or enzymes. Similarly, trapping or chemical deactivation may be used to prevent or substantially reduce the incidence of the proteolytic deactivating agent or agents from reaching the proteolytic agent.

18 Claims, 2 Drawing Sheets

ACTIVE ENZYME PROTECTION SYSTEM FOR AN ELECTROCHEMICAL BIOSENSOR

REFERENCE TO RELATED APPLICATIONS

This application claims the benefit of U.S. Provisional Application No. 62/589,639 entitled "Active Enzyme Protection System for an Electrochemical Biosensor" filed Nov. 22, 2017, which is incorporated by reference in its entirety.

BACKGROUND

Biosensor systems provide an analysis of a biological fluid sample, such as whole blood, serum, plasma, urine, saliva, interstitial, or intracellular fluid. The systems generally include a measurement device that analyzes a sample residing in a test sensor. The sample usually is in liquid form. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the treatment of physiological abnormalities or insufficiencies. For example, a diabetic individual may use a biosensor system to determine the A1c level in whole blood for adjustments to diet and/or medication.

Biosensor systems may be designed to analyze one or more analytes and may use different volumes of biological fluids. Some systems may analyze a drop of whole blood, such as from 0.25-15 microliters ($\mu L$) in volume. Biosensor systems may be implemented using bench-top, portable, and like measurement devices. Portable measurement devices may be hand-held and allow for the identification and/or quantification of one or more analytes in a sample.

Electrochemical biosensor systems usually include a measurement device having electrical contacts that connect with the electrical conductors of a test sensor. The conductors may be made from conductive materials, such as solid metals, metal pastes, conductive carbon, conductive carbon pastes, conductive polymers, and the like. The electrical conductors connect to working and counter electrodes and may connect to reference and/or other electrodes that contact the sample. One or more electrical conductors also may contact the sample to provide functionality not provided by the electrodes.

The measurement device of an electrochemical biosensor system applies an input signal through the electrical contacts to the electrical conductors of the test sensor. The electrical conductors convey the input signal through the electrodes into the sample. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

The test sensor of the electrochemical biosensor system has an inlet to introduce the sample and one or more isolated flow paths to direct the sample from the inlet to one or more electrode pairs for analysis. The one or more isolated flow paths are formed between a substrate and a cover. The one or more isolated flow paths may be formed by indentations formed into the substrate, cover, or both, or by a spacer residing between the substrate and the cover including channels through which the sample flows. The substrate, cover, and spacer are generally formed from polymeric materials, with glass or ceramics substituted in some instances. The substrate, cover, and spacer are generally laminated using heat or light energy, but also may be formed as a unit. At least one of the electrode pairs in the one or more isolated flow paths may be energized in the presence of an active enzyme or other species to generate an analyte specific portion of the output signal. Additional reagents that act on the sample may be incorporated into the test sensor between the electrode pair and the inlet of the test sensor.

In electrochemical biosensor systems, the analyte concentration of the sample is determined from an electrical signal generated by an oxidation/reduction or redox reaction of the analyte or a measurable species responsive to the analyte concentration when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles.

An active enzyme or similar species may be added to the sample to enhance the electron transfer from the analyte during the redox reaction. The active enzyme or similar species may react with a single analyte, thus providing specificity to a portion of the generated output signal. A redox mediator may be used as the measurable species to maintain the oxidation state of the active enzyme and/or assist with electron transfer from the analyte to an electrode. Thus, during the redox reaction, an active enzyme or similar species may transfer electrons between the analyte and the redox mediator, while the redox mediator transfers electrons between itself and an electrode of the test sensor.

The test sensor includes one or more electrode pairs including one or more active enzymes for analysis. At least one of the electrode pairs may be energized in the presence of an active enzyme or other species to generate an analyte specific portion of the output signal. Additional reagents that act on the sample may be incorporated into the test sensor between the electrode pair and the inlet of the test sensor, such as proteolytic agents and lysing agents. Additional reagents also may be incorporated with the active enzyme, if they do not substantially adversely affect the activity of the active enzyme.

Electrochemical biosensor systems relying on an active enzyme to provide analyte specificity to the output signal measured between an electrode pair are generally limited in their reaction chemistry to reagents that will not substantially degrade or denature the active enzyme. Such systems also may be limited in their reaction chemistry to reagents that will not degrade other sensitive species, such as proteolytic agents that reduce the length of protein chains.

Agents that adversely affect the activity of the enzyme include lysing agents that open the cell wall of red blood cells and proteolytic agents that reduce the length of amino acid chains. Such agents may be thought of as active enzyme deactivating agents. Lysing agents also may adversely affect the activity of the proteolytic agents. However, these agents generally cannot be used in combination for electrochemical analysis due to the need to maintain sufficient active enzyme and/or proteolytic activity for the analysis of the sample. For example, while lysing agents may be desirable to lyse red blood cells so an analysis may be directly performed on a whole blood sample without a pre-lysing treatment prior to the analysis, lysing agents will substantially degrade many active enzymes and proteolytic agents if not adequately isolated.

An example of this problem is addressed in U.S. Pat. No. 8,673,646 to Yuan, where a greater than 1:20 dilution of the sample with multiple pre-reactions are performed before the sample is introduced to the test sensor. Thus, the whole blood sample is subjected to multiple dilutions and isolated reactions before being introduced to the test sensor for electrochemical analysis.

As seen from the above description, there is an ongoing need for simple and efficient devices and materials permitting the use of incompatible reaction chemistries in electrochemical biosensor systems. The devices and materials of the present invention overcome at least one of the disadvantages associated with conventional electrochemical test sensors that cannot analyze undiluted blood samples directly, without prior dilution, pretreatment, and the like before introducing the sample into the electrochemical test sensor of the biosensor system.

BRIEF DESCRIPTION OF THE FIGURES

The invention can be better understood with reference to the following drawings and description. The components in the figures are not necessarily to scale, emphasis instead being placed upon illustrating the principles of the invention.

SUMMARY

The invention provides a method of electrochemically analyzing an undiluted whole blood sample with a test sensor, the method including contacting a whole blood sample with a proteolytic agent at a second chemical reaction zone; then transferring the sample to a protease inactivation zone; reducing the activity of the proteolytic agent by altering the chemistry of the sample at the protease inactivation zone; then transferring the sample from the protease inactivation zone to an electrochemical reaction zone; then contacting the sample with an active enzyme that selectively undergoes a redox reaction with an analyte in the sample to produce a measurable species; and electrically altering the oxidation state of the measurable species at an electrode pair in response to an applied potential to generate an output signal component responsive to the analyte concentration of the sample.

Other systems, methods, features and advantages of the invention will be, or will become, apparent to one with skill in the art upon examination of the figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

DETAILED DESCRIPTION

Immobilization zones through which a sample flows before reaching the proteolytic agents and/or active enzyme and associated electrode/s of an electrochemical test sensor may be used to trap or chemically deactivate active enzyme and/or proteolytic agent deactivating agents. Through either trapping or chemical deactivation, the immobilization zones substantially prevent the enzyme deactivating agents from reaching, and thus reducing the activity of the active enzyme or enzymes. Similarly, trapping or chemical deactivation may be used to prevent or substantially reduce the incidence of the proteolytic deactivating agent or agents from reaching the proteolytic agent. Immobilization zones may take the form of an immobilized matrix, an interference reduction matrix, a protease inactivation zone, and combinations thereof.

Figure 1:
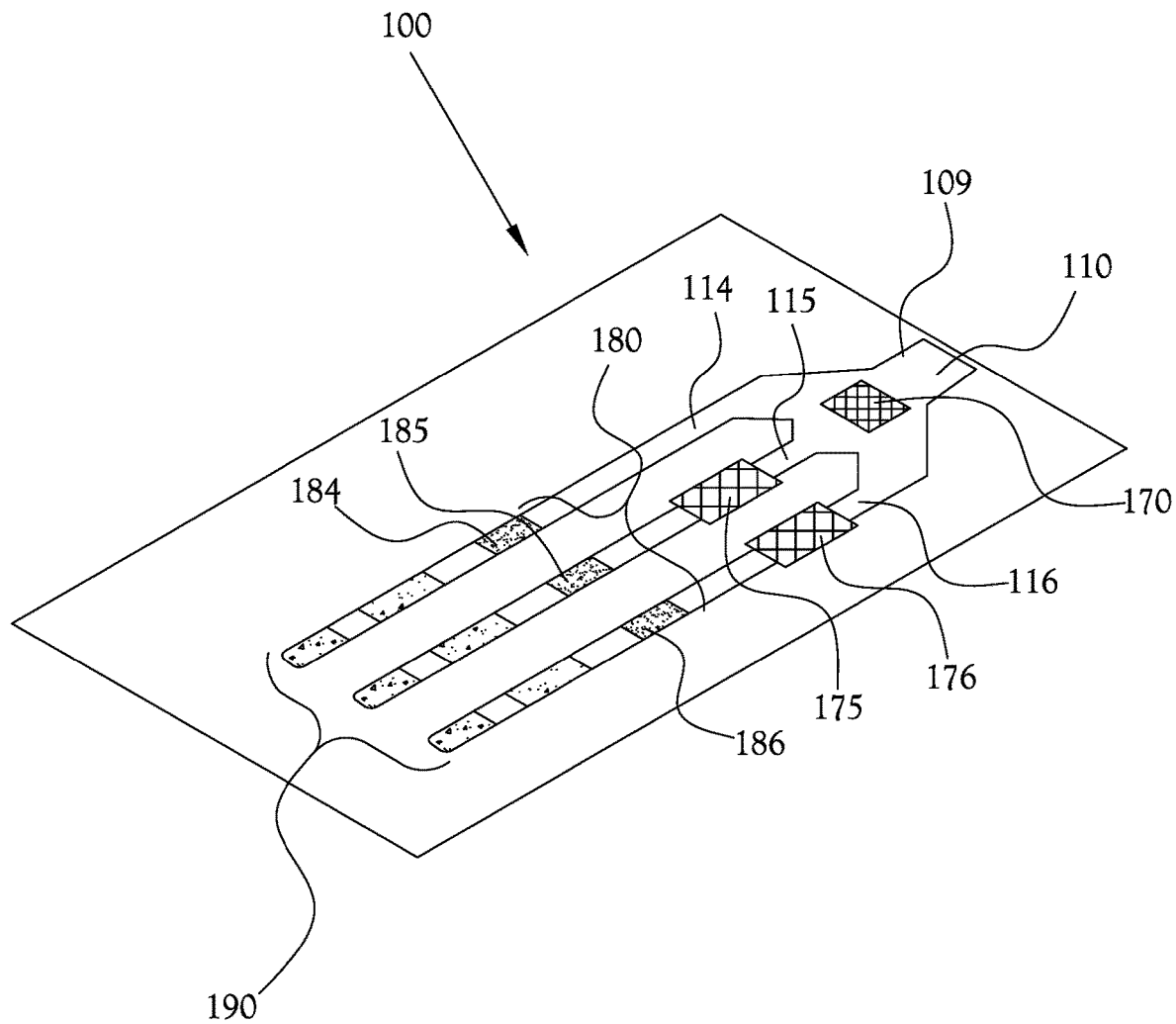
FIG. 1 represents the sample flow channels of a multi-channel electrochemical test sensor

FIG. 1 represents the sample flow channels of a multi-channel electrochemical test sensor 100. The test sensor 100 includes a common flow inlet 110. The common flow inlet 110 branches to form the isolated flow paths 114-116. For the test sensor 100, a liquid sample entering the test sensor 100 passes through the common flow inlet 110 before contacting the first chemical reaction zone 170 and branching from the common flow inlet 110 into a total of three isolated flow paths 114-116. The sample then passes through one or more second chemical reaction zones 175, 176 before contacting protease inactivation zones 180. The sample then reaches electrical reaction zones 190. The constituents and chemistry of the sample may be altered as the sample flows thought the chemical reaction zones and the immobilization zones.

The first and second chemical reaction zones may be physically separated by 4 to 30 millimeters, preferably by 8 to 25 millimeters, and more preferably by 15 to 20 millimeters. The second chemical reaction zones may be physically separated from the protease inactivation zones 185, 186 by 2 to 20 millimeters, preferably by 4 to 10 millimeters, and more preferably by 5 to 8 millimeters.

The sample may reside at the first chemical reaction zone from 0.5 to 2.5 seconds and preferably from 1.0 to 2.0 seconds before transferring to the second chemical reaction zone. The sample may reside at the second chemical reaction zone from 1 to 4 seconds and preferably from 2 to 3 seconds before transferring to the protease inactivation zones 185, 186. The sample may reside at the protease inactivation zones 180 from 0.5 to 1.5 seconds and preferably from 0.8 to 1.2 seconds before transferring to the electrochemical reaction zones 190.

A first chemical reaction zone 170 provides the first chemical reaction zone through which the sample flows. The first chemical reaction zone 170 resides in the common flow inlet 110, but could reside in a different "upstream" position from the electrical reaction zones 190. The first chemical reaction zone 170 includes an immobilized lysing matrix. The immobilized lysing matrix includes a web or supporting viscous mass to immobilize a lysing agent.

The web of the immobilized lysing matrix may be a fibrous polymeric structure in a dried or semi-dried state. The web of the immobilized lysing matrix may be formed from woven polyester, such as the PES 18/13 matrix commercially available from SaatiTech Somers, N.Y. 10589, having a Part No. 7-255-40, or from a PET 255-micron 40% open area woven matrix as available from Sefar, Hinterbissaustrasse 129410 Heiden, Switzerland.

The web of the immobilized lysing matrix may be replaced with a supporting viscous mass, including fumed silica, such as CABOSIL™, glass beads, glutaraldehyde, and other viscous polymeric materials that are non-chemically reactive with the constituents of the analysis, but that hold a lysing or other agent that would deactivate an active enzyme or proteolytic agent.

The first chemical reaction zone 170 includes a lysing or other agent that deactivates active enzymes, proteolytic agents, or other "downstream" species that would be adversely affected by an "upstream" deactivating agent entering the sample and flowing downstream. The lysing or other deactivating agent preferably resides on a first side ("top") of the web.

Example lysing agents include Saponin, cetyltrimethylammonium bromide (CTAB), tetradecyltrimethylammonium bromide (TTAB), Triton X-100, Tween agents (e.g., Tween 20), sodium dodecyl sulfate (SDS), polyoxyethylene lauryl ethers (POEs), Nonidet P-40 (NP-40), amphoteric surfactants, such as AMMONYX® Lo Special, Sodium Deoxycholate, Pancreatic Phospholipase, and the like. For example, a specific chemical reaction zone 170 may include a 0.3% Saponin concentration (weight saponin/weight web).

The first chemical reaction zone 170 also includes an interference reduction matrix that reduces lysate interference from lysed red blood cells, such as arising from glutathione and catalase interference. The interference reduction matrix preferably resides on a second side ("bottom") of the web. Thus, when the sample passes through the first chemical reaction zone 170, the sample first contacts the first side of the web and then contacts the second side of the web. In this manner, the first side of the web may lyse the red blood cells while the bottom of the web may reduce the interference that would otherwise arise from the constituents released from the lysed red blood cells during later stages of the analysis.

The interference reduction matrix includes one or more red blood cell (RBC) constituent interference reducers, such as sodium azide, Dess-Martin periodinane, N-ethyl maleimide, sodium iodoacetate, sodium periodate, and N-chloro 4-methylbenzenesulfonamide salt. Presently, sodium azide is the preferred interference reducer. The RBC interference reducer irreversibly chemically alters glutathione and catalase and renders them inert to downstream active enzyme, protein cleaving agents, and the like.

The interference reduction matrix also includes one or more thickening agents, such as polyvinyl alcohol (PVA), hydroxyethylcellulose (e.g. NATROSOL™), poly(ethylene oxide) (PEO), and the like that prevents the one or more RBC interference reducers from entering the sample and flowing downstream. Presently, a weight ratio of approximately 1 2(PVA):0.5-1.5(Natrasol):0.5(PEO) is preferred; however, other thickening agents in different ratios may be used depending on the constituents of the analysis.

The components used in the interference reduction matrix are chemically compatible with the RBC interference reducer and the analysis. Preferably, the interference reduction matrix irreversibly chemically alters and thus renders inert at least 70%, preferably at least 80%, and more preferably at least 90% of the otherwise downstream chemistry deactivating constituents released from the lysed red blood cells.

Second chemical reaction zones 175, 176 provide second chemical reaction zones through which the sample flows after crossing the first chemical reaction zone 170. The second chemical reaction zones 175, 176 reside downstream of the common flow inlet 110, but upstream of protease inactivation zones 180 and the electrical reaction zones 190. The second chemical reaction zones 175, 176 include reagents that would be deactivated by one or more reagents present in the first chemical reaction zone 170 and that may deactivate the active enzyme if they were to reach the electrical reaction zones 190.

The second chemical reaction zones 175, 176 may include a protein cleaving reagent sufficient to reduce the length of at least one peptide (amino acid) chain in the sample. Preferred proteolytic agents include DISPASE™ I (neutral protease, grade I), commercially available from Roche Diagnostics USA, Indianapolis, Ind.; proteinase K; NEP-201 or NEP-801 Neutral Proteinase, commercially available from Toyobo, 2-8, Dojindo Hama 2-chome, Kita-ku, Osaka 530-8230 Japan; pepsin; renin; and papain. Of these proteolytic agents, NEP-201 Neutral Proteinase is presently preferred.

Instead of proteolytic agents, the second chemical reaction zones 175, 176 may be used to isolate an oxidizing enzyme from its reducing counterpart. For example, when glutamate oxidase and glutamate reductase are both used on the same test sensor to analyze reaction byproducts, the oxidase and reductase enzymes must be physically separated to prevent them from repeatedly oxidizing and reducing each other in a "closed-loop", as opposed to acting on the sample constituents. This necessary physical separation would be achieved by depositing one form of the enzyme at the second chemical reaction zones 175, 176, while the other enzyme form would be deposited at the electrical reaction zones 190. Thus, the sample would contact the first form of the enzyme at the second chemical reaction zones 175, 176 before contacting the electrical reaction zones 190 where the second form of the enzyme is contacted by the sample.

The second chemical reaction zones 175, 176 immobilize the desired reagent, whether proteolytic or an active enzyme. The desired reagent may be immobilized at the second chemical reaction zones 175, 176 using a polymeric binder, or a polymeric binder in combination with a web or supporting viscous mass, as previously described.

Polymeric binders include polyvinyl alcohol (PVA), polyvinylpyrrolidone (PVP), and other viscous polymeric materials that are compatible with the other constituents of the analysis and do not significantly adversely affect the active enzyme or enzymes at the electrical reaction zones 190. Unlike the thickening agents of the first chemical reaction zone 170, the polymeric binder of the second chemical reaction zones 175, 176 preferably includes a mixture of two polymers, with one polymer being more hydrophilic than the other.

Presently, a blend of PVA and PVP is preferred as the polymeric binders, with PVP being the more hydrophilic of the two. More preferred is a blend of PVA and PVP in an approximate 2:1 ratio by weight. Thus, while PVA may be used as a thickening agent in the first chemical reaction zone, if used in the second chemical reaction zone, it is combined with a more hydrophilic polymer. Other polymeric binders may be used depending on the reagents present in the first and/or second chemical reaction zones.

In the instance where a protein cleaving reagent is immobilized at the second chemical reaction zones 175, 176, the pH of the second chemical reaction zones 175, 176 may be higher than neutral, such as from 8 to 9. Thus, the pH of the second chemical reaction zones 175, 176 may be approximately 8.

The protease inactivation zones 180 are downstream of the first chemical reaction zone 170, but upstream of the electrical reaction zones 190. The protease inactivation zones 180 are physically separated from the first and optional second chemical reaction zones and the electrical reaction zones 190. The protease inactivation zones 180 reside between the first chemical reaction zone 170 and the electrical reaction zones 190, and may or may not reside between any optional second chemical reaction zones and the electrical reaction zones 190. In FIG. 1, the individual protease inactivation zones 184, 185, and 186 are provided in the isolated flow paths 114, 115, and 116, respectively. However, other zone arrangements are possible.

The protease inactivation zones 180 alter the chemistry of the sample to inactivate the protease and may be pH adjustment zones, chemical inactivation zones, or a combination thereof. pH adjustment zones include at least one buffer, a polymeric binder, or a polymeric binder in combination with a web or supporting viscous mass, as previously described in the context of the second chemical reaction zones 175, 176. Chemical inactivation zones include at least one protease chemical inactivator, a polymeric binder, or a polymeric binder in combination with a web or supporting viscous mass, as previously described in the context of the second chemical reaction zones 175, 176.

The at least one buffer of a pH adjustment zone is selected to provide the desired pH for the active enzyme at the electrical reaction zones 190. For example, if the pH of the second chemical reaction zones 175, 176 is approximately 8, and if a pH of 6.8 is desired at the electrical reaction zones 190, a suitable buffer would be Chess to reduce the pH of the sample from approximately 8 to 6.8. Other suitable buffers could be those as provided by Sigma-Aldrich and similar sources that achieve the desired pH at the electrical reaction zones 190 while maintaining compatibility with the analysis and sample constituents.

By altering the chemistry of the sample through changing the pH of the sample, the protease inactivation zones 180 deactivate or substantially reduce the activity of a reagent in the sample released from the second and optionally first chemical reaction zones. In the instance of a protein cleaving mesh for the second chemical reaction zones, for example, the pH adjustment zones may include a buffer that alters the pH from the high pH, such as greater than eight to nine, to a pH closer to neutral, such as from 6 to 7. Thus, the pH of the pH adjustment zones may be approximately 6. The pH adjustment zones may alter the sample pH to be compatible with the chemistry and active enzyme/s of the later electrical reaction zones 190.

By altering the chemistry of the sample through contacting the sample with a chemical inactivator, the protease inactivation zones 180 deactivate or substantially reduce the activity of a reagent in the sample released from the second and optionally first chemical reaction zones. In the instance of a protein cleaving mesh for the second chemical reaction zones, for example, the chemical inactivation zones may include a chemical inactivator such as ethylenediaminetetraacetic acid (EDTA), ferric chloride, polyoxyethylene (23) lauryl ether (Brij 35), and polyethylene glycol sorbitan monolaurate (TWEEN 20), with EDTA being more preferred. The chemical inactivator is selected to be compatible with the chemistry and active enzyme/s of the later electrical reaction zones 190.

Preferably the protease inactivation zones 180 reduce the activity of a proteolytic agent by at least 30%, preferably by at least 70%. For example, a proteolytic agent that is ~90% active at pH ~8 and is ~60% active at pH ~6, undergoes a greater than 30% reduction in activity at the lower pH of the pH adjustment zones 180. Similar reductions may be observed with the chemical inactivators.

The electrochemical reaction zones 190 include one or more active enzymes that are protected from degradation. Active enzymes include fructosyl amino oxidase (FAOX/FAOD), creatinine deiminase, creatinine iminohydrolase, glutamate oxidase, pyruvate oxidase, and the like. The temperature of the electrochemical reaction zones 190 may be reduced by at least 10, preferably at least 15 degrees C. in relation to the temperature of the second chemical reaction zones 175, 176 to further reduce degradation of the active enzyme. For example, a proteolytic agent that has a 50% activity at a second chemical reaction zone heated to 60 degrees C. may drop to 20% at 42 degrees C.

Figure 2:
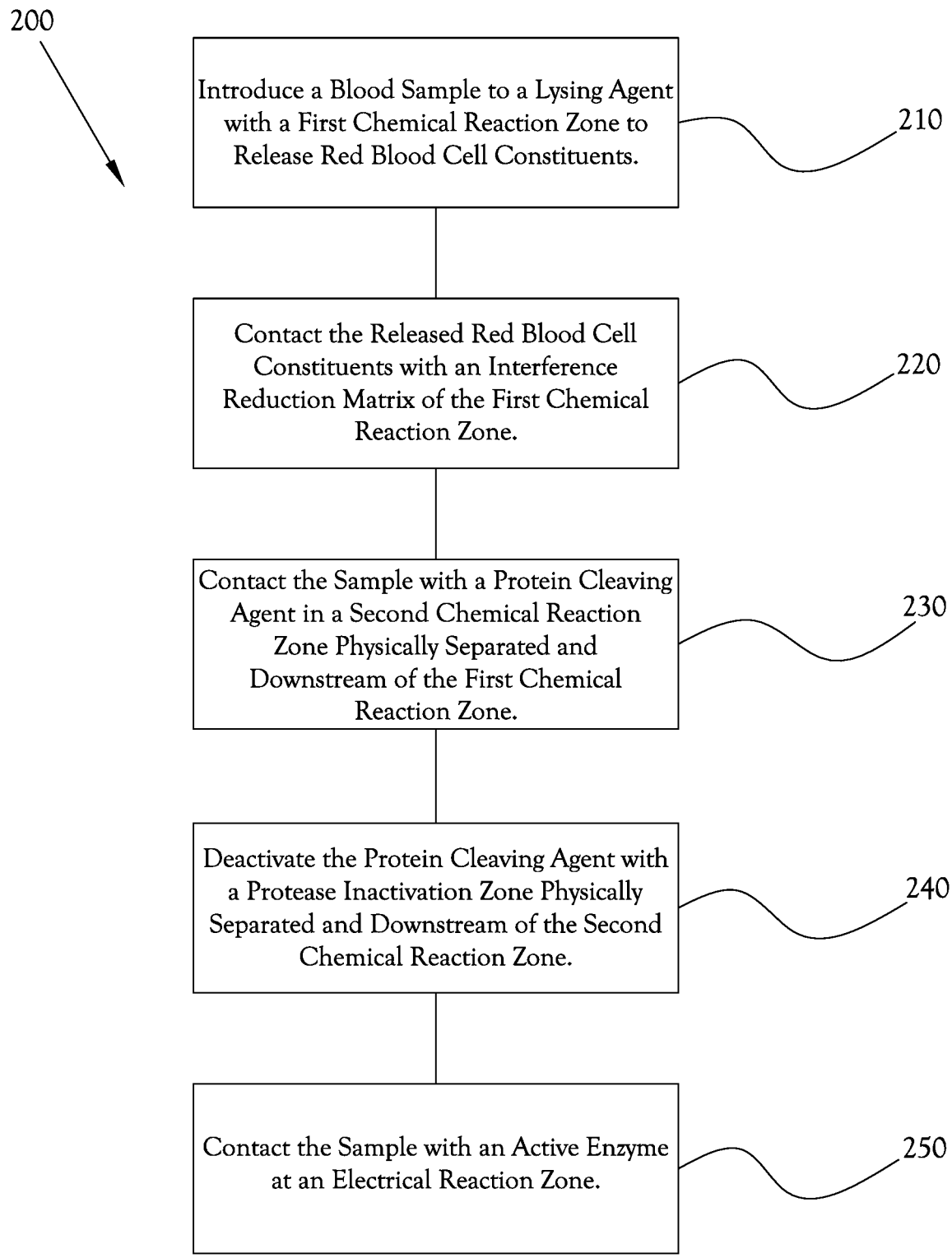
FIG. 2 represents a method of protecting the active enzyme of a test sensor having a first chemical reaction zone that lyses a blood sample.

FIG. 2 represents a method 200 of protecting the active enzyme of a test sensor having a first chemical reaction zone that lyses a blood sample. In 210, a first chemical reaction zone introduces a lysing agent to the sample. In 220, an interference reduction matrix of the first chemical reaction zone deactivates the lysing agent. In 230, a second chemical reaction zone physically separated from and downstream of the first chemical reaction zone introduces a protein cleaving agent to the sample. In 240, a protease inactivation zone physically separated and downstream of the second chemical reaction zone deactivates the protein cleaving agent. In 250, the sample then reaches the active enzyme of the test sensor electrical reaction zones.

The following examples illustrate one or more preferred embodiments of the invention. Numerous variations may be made to the following examples that lie within the scope of the invention.

EXAMPLES

Example 1: Preparation of a First Chemical Reaction Zone Including an Immobilized Lysing Matrix and an Interference Reduction Matrix Buffer Preparation: Ches Buffer—Sigma C2885 and Trizma Buffer—Sigma T1503 were used, with the Ches buffer being preferred. In one instance, 10.4 grams of Ches Buffer was added to 400 mL of distilled water and dissolved by stirring. The pH was adjusted 8.2 to provide a total solution volume of 500 mL.

Lysing Reagent and Interference Reduction Matrix Reagents: Poly(ethylene glycol) (PEG) m.w. 6000—Sigma 581260, 2-Hydroxyethyl cellulose 250 G (HEC)—Ashland Inc. Covington, Ky., Saponin—Sigma 558255, Tetradecyltrimethylammonium bromide (TTAB)—Sigma T4762, Cetrimonium bromide (CTAB)—Sigma H9151, Ammonyx-LO-Stepan Co. Northfield, Ill., Dess-Martin periodinane (Dess-Martin)—Sigma 274623, N-Ethylmaleimide (NEM)—Sigma-E1271, Sodium Azide—Sigma S2002, Avicel RC-591, Avicel Cl-611F, —FMC Health and Nutrition Philadelphia, Pa., CaboSil 720—Cabot Corporation Boston, Mass., Vinac XX-210—Ashland Inc. Columbus, Ohio, woven polyester mesh PES 18/13—Saarti, Saaticare PES 18/13, SaatiTech Somers, N.Y.

Lysing Reagent: One gram of the PEG was added to 90 mL of the Ches buffer solution and mixed until dissolved. Next, 0.5 grams of HEC was added to the solution and mixed until dissolved. Lysing agents for the matrix included: TTAB, CTAB, Ammonyx-Lo, and Saponin with Saponin being preferred. In the case of Saponin, 0.6 grams was added to the solution. The mixture was stirred for 2 hours to disperse the Saponin. The pH was adjusted to 8.0, and the total solution volume increased to 100 mL. The resulting mixture was sprayed on the top side of a polyester mesh.

Interference Reduction Matrix: One gram of PEG was added to 90 mL of the Ches buffer and stirred until dissolved. Next, 0.5 grams of HEC was added to the solution and stirred until dissolved. Next, 0.2545 grams of Dess-Martin, 0.0375 NEM, and 0.5 grams of Sodium Azide were added and stirred. While stirring 0.05 grams CaboSil 720, 0.10 grams of Avicel Cl-611F, and 0.125 grams of Vinac XX-210 were added. The mixture was homogenized. Then, 0.20 grams of Avicel RC-591 was added and the mixture was again homogenized. The resulting mixture was sprayed on the bottom side of the polyester mesh. Different Temperature Zones through Heating Element Spacing.

Example 2: Preparation of a Second Chemical Reaction Zone

Protein Cleaving Reagents: Trizma—Sigma t4661, Polyvinylpyrrolidone (PVP)—Sigma PVP40, Polyvinyl alcohol (PVA)—Sigma P8136, Avicel Cl-611F, —FMC Health and Nutrition Philadelphia, Vinac XX-210—Ashland Inc. Columbus, Ohio, PA Neutral Protease—NEP201 Toyobo Osaka, Japan, Polyester woven mesh 255 micron/40% open area (mesh)—Sefar Heiden Switzerland.

Preparation of 200 mM Trizma buffer solution: About 12 grams of Trizma buffer was added to 400 mL of distilled water and mixed until dissolved. The pH of the resulting solution was adjusted to a pH of 8.5 and a total volume of 500 mL.

Preparation of Polymer Solution: About 0.5 grams of PVP 40K and 1.5 grams of PVA was added to 90 mL of the previously prepared Trizma buffer and heated with agitation. One gram of Avicel Cl-611F and 0.5 grams of Vinac XX-210 were then added. The pH was adjusted to 8.50 to provide a liquid volume of 100 ml and homogenized.

Enzyme stock solution: Protein cleaving agents include trypsin, and Papain with Neutral Proteinase being preferred. Assuming an enzyme activity of 1000 units/mg and 4 units per sensor, 0.04 grams of protease enzyme was added to 10 mL of the polymer solution. Mix until the enzyme is dissolved in the solution. A polyester mesh was then dipped into enzyme solution and dried at 45° C. for about 20 minutes.

Example 3: Preparation of a pH Adjustment Zone

The pH of the sample lysate/proteolytic product flowing from a protease cleaving mesh matrix is about 7.5 to 9.0. This pH was adjusted to a pH compatible with the pH of the FAOX active enzyme in the reaction zone.

A 200 mM PIPES buffer solution was prepared with PIPES Buffer from Sigma-Aldrich by adding about 12 grams of the PIPES Buffer to 400 mL of distilled water and stirring until dissolved. The pH was adjusted to 7.5 at a total solution volume of 500 mL. About 0.5 grams of HEC was added to the solution and stirred during which time 0.05 grams CaboSil 720, 0.10 grams of Avicel Cl-611F, and 0.125 grams of Vinac XX-210 were added. The mixture was homogenized, and the pH adjusted to 8.0.

Polymer dispense: A Biodot PixSys 3200 dispenser was used to dispense 2 uL of the mixture in the region downstream of the second chemical reaction zone, but before the electrical reaction zones. The test sensors were then dried at 45° C. for about 15 minutes.

The buffer may be replaced with a chemical inactivator to form a chemical protease inactivation zone.

Unless the context clearly dictates otherwise, where a range of values is provided, each intervening value to the tenth of the unit of the lower limit between the lower limit and the upper limit of the range is included in the range of values.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. A method of electrochemically analyzing an undiluted whole blood sample in a test sensor, the method comprising:
   introducing an undiluted whole blood sample to an inlet of a test sensor, the test sensor having at least one isolated flow path;
   contacting the undiluted whole blood sample with a lysing agent at a first chemical reaction zone in the at least one isolated flow path to release red blood cell constituents,
   then contacting the undiluted whole blood sample with an interference reduction matrix that reduces lysate interference,
   then contacting the undiluted whole blood sample with a proteolytic agent at a second chemical reaction zone in the at least one isolated flow path;
   then transferring the sample to a protease inactivation zone in the at least one isolated flow path;
   reducing the activity of the proteolytic agent by altering the chemistry of the sample at the protease inactivation zone;
   then transferring the sample from the protease inactivation zone to an electrochemical reaction zone in the at least one isolated flow path;
   then contacting the sample with an active enzyme that selectively undergoes a redox reaction with an analyte in the sample to produce a measurable species; and
   electrically altering the oxidation state of the measurable species with an electrode pair in response to an applied potential to generate an output signal component responsive to the analyte concentration of the sample.

2. The method of claim 1, where the reducing the activity of the proteolytic agent by altering the chemistry of the sample at the protease inactivation zone reduces the activity of the proteolytic agent by at least 30%.

3. The method of claim 1, where the reducing the activity of the proteolytic agent by altering the chemistry of the sample at the protease inactivation zone reduces the activity of the proteolytic agent by at least 70%.

4. The method of claim 1, where contacting the sample with the lysing agent and contacting the sample with the interference reduction matrix occur sequentially at the first chemical reaction zone.

5. The method of claim 1, where the first chemical reaction zone is separated from the second chemical reaction zone by 4 to 30 millimeters.

6. The method of claim 1, where the second chemical reaction zone is separated from the protease inactivation zone by 2 to 20 millimeters.

7. The method of claim 4, where the interference reduction matrix irreversibly chemically alters the released red blood cell constituents.

8. The method of claim 1, where the sample is present at the first chemical reaction zone from 0.5 to 2.5 seconds before transferring to the second chemical reaction zone.

9. The method of claim 1, where the sample is present at the second chemical reaction zone from 1 to 4 seconds before transferring to the protease inactivation zone.

10. The method of claim 1, where the sample is present at the protease inactivation zone from 0.5 to 1.5 seconds before transferring to the electrochemical reaction zone.

11. The method of claim 1, further comprising reducing the temperature of the electrochemical reaction zone by at least 10 degrees C. in relation to the temperature of the second chemical reaction zone.

12. The method of claim 1, further comprising reducing the temperature of the electrochemical reaction zone by at least 15 degrees C. in relation to the temperature of the second chemical reaction zone.

13. The method of claim 1, where the pH of the second chemical reaction zone is approximately 8.

14. The method of claim 1, where the protease inactivation zone is a pH adjustment zone.

15. The method of claim 14, where the pH of the pH adjustment zone is approximately 6.

16. The method of claim 1, where the protease inactivation zone is a chemical inactivation zone.

17. The method of claim 16, where the chemical inactivation zone comprises a chemical inactivator selected from the group consisting of ethylenediaminetetraacetic acid (EDTA), ferric chloride, polyoxyethylene (23) lauryl ether (Brij 35), polyethylene glycol sorbitan monolaurate (TWEEN 20), and combinations thereof.

18. The method of claim 16, where the chemical inactivation zone comprises ethylenediaminetetraacetic acid.

* * * * *